(12) United States Patent
Cazzini et al.

(10) Patent No.: US 7,164,852 B2
(45) Date of Patent: Jan. 16, 2007

(54) FLUID RESERVOIR WITH INTEGRATED HEATER

(75) Inventors: Karl H. Cazzini, Orchard Park, NY (US); Thomas P. Stewart, Orchard Park, NY (US)

(73) Assignee: Gaymar Industries, Inc., Orchard Park, NY (US)

( * ) Notice: Subject to any disclaimer, the term of this patent is extended or adjusted under 35 U.S.C. 154(b) by 0 days.

(21) Appl. No.: 11/032,827

(22) Filed: Jan. 11, 2005

(65) Prior Publication Data

US 2006/0153549 A1 Jul. 13, 2006

(51) Int. Cl.
*A61F 7/00* (2006.01)
(52) U.S. Cl. .................................. 392/470; 392/478
(58) Field of Classification Search ............... None
See application file for complete search history.

(56) References Cited

U.S. PATENT DOCUMENTS

| | | | | |
|---|---|---|---|---|
| 3,178,559 A | * | 4/1965 | Fogel et al. | 219/527 |
| 4,108,146 A | * | 8/1978 | Golden | 607/104 |

* cited by examiner

*Primary Examiner*—Thor S. Campbell
(74) *Attorney, Agent, or Firm*—Roach Brown McCathy & Gruber, P.C.; Kevin D. McCarthy (57) ABSTRACT

The present invention is directed to a fluid warming container (a.k.a., cassette) having an integrated heating element attached to the container, not the warming device as conventionally done. The heating element provides thermal energy to the fluid contained in the container. The fluid contained in the container is designed to be injected and/or delivered, eventually and normally immediately, into a patient.

44 Claims, 6 Drawing Sheets

FLUID RESERVOIR WITH INTEGRATED HEATER

FIELD OF THE INVENTION

The present invention relates to an apparatus for warming blood and other fluids to a desired temperature prior to introduction of the fluid into a patient.

BACKGROUND OF THE INVENTION

Gaymar Industries, Inc., the assignee of this application, is the assignee of U.S. Pat. No. 5,875,282 (hereinafter referred to as "the '282 patent"). The '282 patent is directed to an apparatus for warming blood and other fluids to a desired temperature prior to introduction into a patient. The blood and other fluids flow through a pathway contained by a bag. That pathway provides high flow performance and normally provides uniform, gradual and energy efficient blood warming. The bag has a pair of guide rails and a warming device has a pair of corresponding apertures that work in conjunction to ensure the bag is properly inserted into the warming device.

The warming device contains at least one, and normally a pair of opposed, identical heater elements, a receptive slot down the middle in a horizontal plane with the possibility of two guide slots, one on each side of the receptive-slot. The optional guide rails align the bag so it can be spaced and located precisely between the two heater elements. The pair of guide rails, integrated into the sides of the bag, is parallel to one another providing sufficient rigidity for easy insertion of the bag, and being sized to allow easy insertion in only the correct orientation. The blood warmer preferably incorporates a microprocessor for precise control of the electric current provided to the heater. Fluid temperature can be measured by contact of a RTD sensor with a thin dielectric surface layer in contact with the bag and located proximal to the fluid outlet and within the heater elements. By monitoring the temperature of the fluid at the outlet of the bag, the temperature controller can compute and provide a visual display of the fluid temperature. In one embodiment, the sensed output temperature is an input parameter to the controller of the heater elements. The device efficiently warms the fluid to about 37.5° C. for anticipated input to a human and, is simultaneously designed to prevent the fluid from exceeding 42° C.

The apparatus disclosed in the '282 patent is a very good fluid warming device but the applicants continue to try to improve it. One improvement is directed to making sure the heating elements are in constant contact with the cassette to ensure the fluid in the fluid path is uniformly heated to the desired temperature. Applicants are unaware of fluid warming apparatuses for fluids designed to enter a patient that are materially distinct from the apparatus disclosed in the '282 patent, except for the following invention.

SUMMARY OF THE INVENTION

The present invention is directed to a fluid warming container (a.k.a., cassette) having an integrated heating element attached to the container, not the warming device as conventionally done. The heating element provides thermal energy to the fluid contained in the container. The fluid contained in the container is designed to be injected and/or delivered, eventually and normally immediately, into a patient.

These and other objects are solved by the present invention. The invention will be understood more fully, while still further objects and advantages will become apparent, in connection with the following detailed description of a preferred embodiment thereof, illustrated in the accompanying drawings.

DETAILED DESCRIPTION OF THE INVENTION

Figure 1:
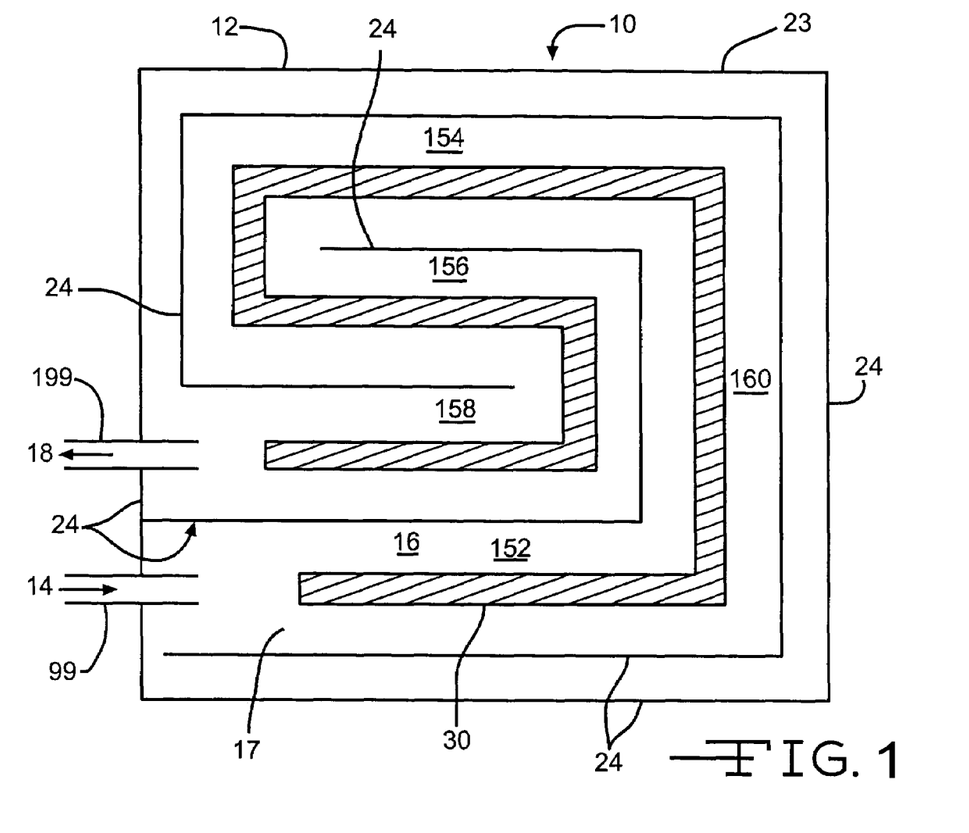
FIG. 1 is a top plan view of a fluid bag of the present invention.
Figure 2:
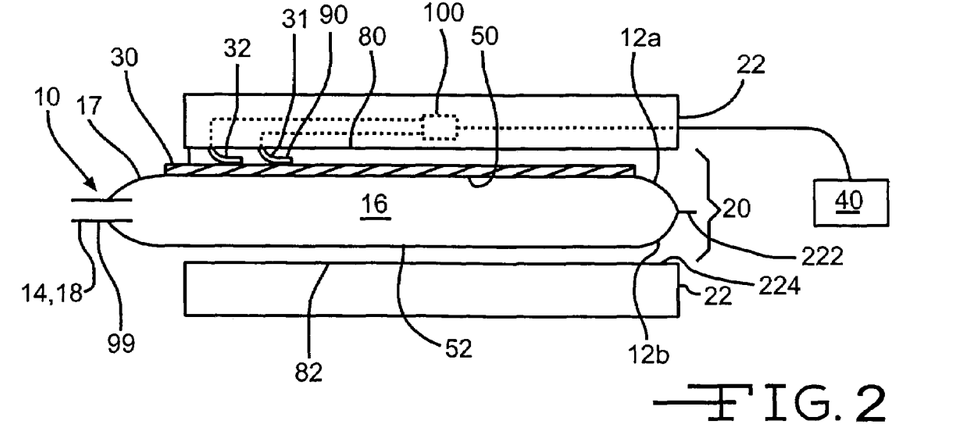
FIG. 2 is cross-sectional view of a fluid bag in a warmer device of the present invention.

The present invention is directed to a heating cassette 10 and alternatively, the heating cassette 10 with fluid compression capabilities. The cassette 10, as shown in FIG. 1, is at least one sheet of fluid impermeable material 12 having a fluid inlet 14, a fluid path 16, and a fluid outlet 18. The cassette 10 is designed to be inserted into a slot 20 of the warmer device 22, as illustrated in FIG. 2.

In one embodiment, the warmer device 22 is identical or similar to the warmer device disclosed in the '282 patent, except for the heater elements and the position of the temperature sensor. Accordingly, we hereby incorporate by reference the entire disclosure of the '282 patent in this application, minus the positions of the heater element and the temperature sensor.

A main difference between the warmer device 22 of the present invention and the warmer device of the '282 patent lies in the position of a heater element 30. In the '282 patent, the heater elements were the upper and/or lower boundary of the slot. The heater element was positioned to contact the exterior surface of the cassette and transfer the heat generated by the heater element to the fluid in the fluid path of the cassette.

The present invention has the heater element 30 as an integrated component of the cassette 10. The heater element 30, in one embodiment, is any conductive material that generates resistance when an electrical current passes through it, and therefore generates heat that is transferred to the fluid in the fluid path 16. Moreover, the conductive material 30 must be capable of being integrated into, within and/or onto the cassette 10 by various methods, including and not limited to printing, embossing, heat sealing, adhesion, polymerizing, or lithographing. These methods are known to those of ordinary skill in the art, and have been used extensively in the field of flexible conductive circuits. Gaymar is unaware of using such technology for warming fluids designed to enter a patient.

The fluid impermeable material 12 must allow thermal energy to transfer into the fluid path for the first embodiment wherein the conductive element is within and/or on the material 12. Alternatively, the material 12 must allow an electrical current to pass through at least a portion of the fluid impermeable material 12 if the conductive element 30 is in the interior of the material 12. An example of, and not limited to such, the fluid impermeable material is thin (like four thousandth of an inch (0.004") thick) polyethylene. The fluid impermeable, thermal energy transfer material 12 may be a single sheet folded over 23 and sealed, by various known methods (heat welding, adhesive, sonic welding), at predetermined portions 24 along the edges and within the interior section to form the fluid path 16 as shown in FIG. 1. Alternatively, the material 12 may comprise at least a first sheet 12a and a second sheet 12b, as shown in FIG. 2, that are sealed, by various known methods, at predetermined portions along the edges and within the interior section to form the fluid path 16. In any case, the material 12 is integrated with a conductive material 30.

Figure 3A:
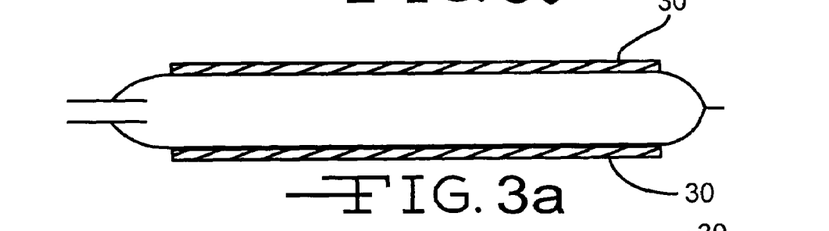
FIGS. 3a–e are top plan views or cross-sectional views of various embodiments of the fluid bag of the present invention.
Figure 3B:
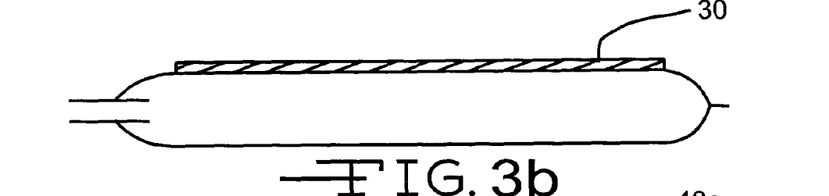
Figure 3C:
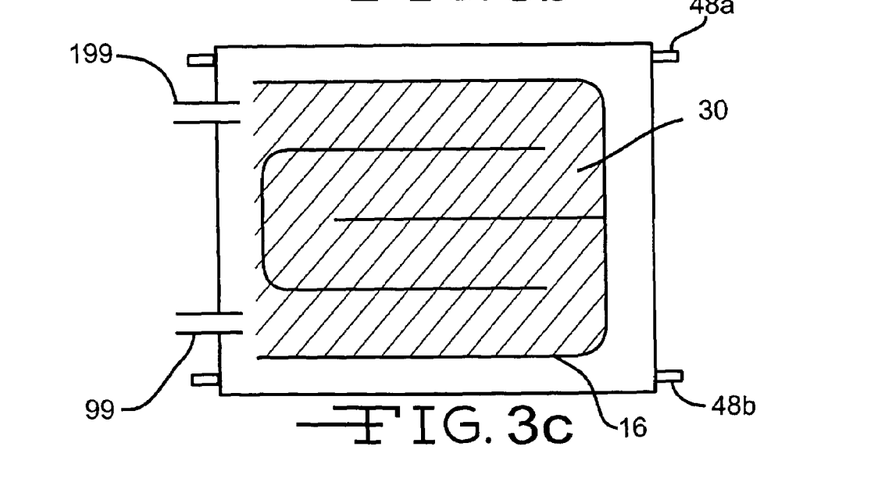

The heating element 30 can overlie the entire exterior surface 17 of the cassette 10 as shown in FIGS. 3a and e, the entire exterior surface 17 of one side of the cassette as shown in FIG. 3b, the entire exterior surface 17 of the fluid path 16 on one or both sides of the cassette 10 as illustrated in FIGS. 3c and 3a and b, predetermined portions of exterior surface 17 of the fluid path 16 on one or both sides of the cassette as illustrated in FIGS. 1 and 3a and b, or combinations thereof.

The heating element 30 can be incorporated into the fluid impermeable material. Such conductive fluid impermeable materials are known to those of ordinary skill in the art. Examples of such conductive films can be found at, and not limited from such location, Bennett and Bennett in Springfield, Ohio. For example, a conductive polyethylene bag can be made from a single layer of carbon-loaded polyethylene. The conductivity does not depend on humidity. It is non-abrading, does not contaminate components or fluids it comes in contact with and is groundable.

Figure 3D:
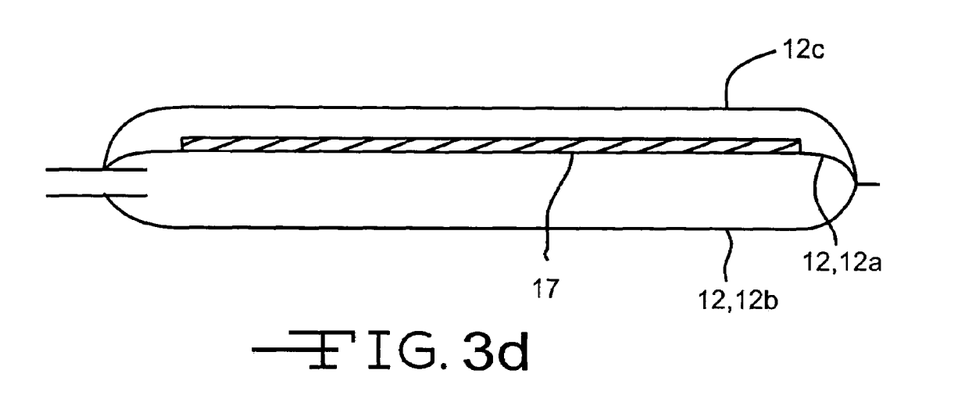
Figure 3E:
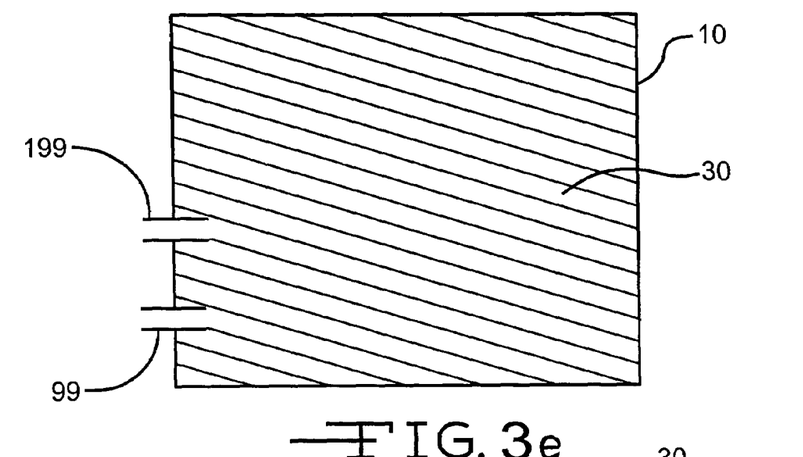

The heating element 30 can also be enclosed between the exterior surface 17 of the fluid path 16 and a third sheet 12c. The third sheet 12c is designed to provide further protection to the heating element 30, as illustrated in FIG. 3d. The third sheet 12c can be sealed to the single sheet 12, the first sheet 12a, the second sheet 12b or combinations thereof, at the edges, at predetermined portion of the edges, and/or at the interior surfaces, or combinations thereof. In this alternative embodiment, the heater element 30 could be a heat transfer fluid, like a Therminol fluid.

In yet another embodiment, the heating element can be on the interior surface 170 of the fluid path 16. In such embodiment the heating element 30 is printed on the surface 170. Alternatively, the heating element could also be within and/or on the impermeable material to assist in the transfer of the energy source, in most cases electricity and/or use of inductive heat, to the heating element.

To allow the present invention to properly operate with a conductive heating element 30, the warming device 22 has at least one electrical contact 32, or direct wired, designed to transmit an electrical current to the integrated heater element 30. The electrical contact 32 can be a spring or other device, actuating or not, that contacts the heater element 30 when the heating cassette 10 is positioned within the slot 20. In one embodiment, the electrical contact 32 is not designed to materially block and/or materially restrict the flow of the fluid within the fluid path 16. The electrical contact 32 is merely designed to merely contact the heater element 30, as shown in FIG. 1, to allow electricity to travel from the warming device 22 to the heater element 30 integrated with the heating cassette 10.

Figure 4:
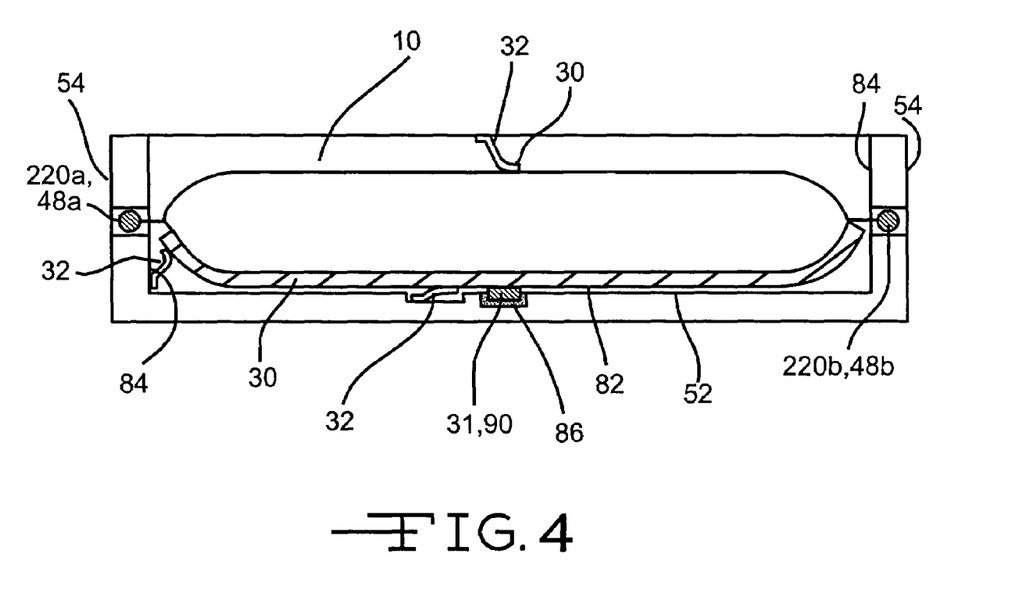
FIG. 4 is an alternative embodiment of FIG. 2.

The electrical contact 32 can be positioned anywhere in relation to the heater element 30. There can even be multiple electrical contacts 32. The electrical contacts 32 can be positioned to contact (i) the top surface 50 of the cassette 10 if the heater element 30 is below the top surface 80 of slot 20 as shown in FIG. 1, (ii) the bottom surface 52 of the cassette 10 if the heater element 30 is over the bottom surface 82 of the slot 20 as illustrated in FIG. 4, (iii) the side surface 54 of the cassette 10 as illustrated in FIGS. 3 and 4 if the heater element 30 contacts or is adjacent to the corresponding side surface 84 of the slot 20; or combinations thereof.

When operating, the warming device 10 interconnects to an electrical source 40. The electrical source 40 delivers an electrical current to the warming device 10, which in turn delivers the current to the electrical contact and then to the heater element 30.

How is the temperature controlled in the warming device? The warming device uses a plurality of devices to control the temperature. For example, it uses a sensor 90 as a resistance temperature detector (RTD). The sensor 90 can be positioned anywhere on or over the exterior 17 of the fluid path 16, the tubing into or out of the cassette, and/or the heater element 30. The sensor 90 can be thermally insulated from the heating element 30 by insulation using suitable materials or by physical location distal to the heater element, for example and not limited to three layers 92 of Teflon.R™. The sensor 90 is can be positioned on a second spring or a second actuating/non-actuating device 31 (see FIG. 4) that can contact the desired portion of the cassette 10, and/or tubing. The sensor 90 is normally attached to the second device 31 by a layer of high temperature adhesive 86. The normal, but not to be limited to such dimensions, total distance from sensor 90 to the fluid in the cassette is ten thousandths of an inch (0.010"). Suitable sensors are well known and available in the art. (For example, a suitable sensor is manufactured by Minco Products Inc., of Minneapolis, Minn.)

In FIG. 1, the applicants illustrate a conventional fluid path used in fluid cassettes. The design illustrated in FIG. 1 is known as a counter-flow fluid path. That fluid path has been determined to provide a desired thermal exchange between the fluid and the heater elements; and the fluid exiting the cassette and the fluid entering the cassette 10. By no means is the present fluid path design limited to this counter-flow design. In particular, the fluid path can be serpentine, or even, though not normally desired, a straight path or random path, but these paths can be used.

In any case, the counter-flow fluid path can be described as follows: The cold flow of fluid enters the cassette 10 at inlet port 14. Once the fluid is within the fluid path 16, a preferred fluid path entails having the fluid traverse down path 152. In relation to the fluid entering the inlet 14, the fluid turns left 90° to proceed down path 160. Path 160 and the inlet 14/outlet 18 are on the opposite sides of the cassette 10. From path 160, the fluid turns another left 90° to enter path 154. Path 154 directs the fluid to the front of the cassette (side of the inlet and outlet 14, 18). Near the front of the cassette, the fluid again turns left. This time the turn is 180° into path 156. Path 156 directs the fluid toward path 160. Prior to reaching path 160, the fluid turns 180° to the right into path 158. From path 158, the fluid is directed toward the outlet 18.

From outlet 18, the fluid can be directed toward a second warmer unit, or alternatively to a patient.

Fluid path 158 is normally the warmest fluid path portion and is located in the middle of the coldest path portion 152 and a colder path portion 156, causing a thermal counter balance of energy. The sensor 90 is normally located near outlet 18 where fluid exits the heat exchanger 16 to ensure the fluid's temperature is at or near the desired predetermined temperature prior to entering the patient. The automatic temperature controller stabilizes at a preset temperature limit causing a thermal counter balance with the energy reservoir.

The described sensor in its specific location is one of many keys to the thermal control system. The sensor can be a simple on/off switch to an algorithmic controlled sensor. One example, which is in the middle of those two examples is a thermal feedback system used is a proportional, integral, derivative (PID) temperature controller. This is a control mode with three functions. The "proportional action" dampens the system response. "Integral" corrects for droop. "Derivative" seeks to prevent overshoot and undershoot. The sensor input sampling rate is, for example and not limited to, 10 samples/second of the fluid's temperature exiting the cassette 10. A thermal counterbalance of fluid exists from the cassette 10 compared to a predetermined set temperature which is the feedback signal to a PID temperature controller, which is set forth in the '282 patent. The temperature controller will adjust and replenish any energy lost to the cassette 10 through the heater element 30.

The primary PID temperature controller maintains an output temperature of approximately 35° to 40° C. in the fluid over the flow range of 10 to 300 ml/min for 10° C. fluid input. For 20° C. or above, the fluid input may be warmed to a flow rate of 500 ml/min. If the primary controller senses a fluid temperature above 43° C. an audible alarm will also sound and cut off power to the energy reservoir. The unit will await a fluid temperature drop below 43° C., or any other desired temperature desired by the user, before turning off the audible alarm.

When the primary controller senses a fluid temperature below 34° C. an audible alarm will also sound and automatically adjust power to the energy reservoir, awaiting fluid temperature rise above 34° C. before turning off the audible alarm.

The temperature controller is recognized to be regularly available in the art. The PID primary temperature controller 100 is, for example, a series 935 auto tuning controller manufactured by Watlow Control of Winona, Minn.

If the cassette temperature reaches a predetermined temperature, an audible alarm will sound and power will cut off to the heating element 30 and PID controller. The audible alarm can be programmed to be terminated, for example, by removing the power cord from the wall socket. A safety cut-out switch is well known and available in the art.

As shown in the circuit diagram in FIG. 5 of the '282 patent, if there is a catastrophic failure, and the temperature of the energy reservoir rises to 45° C., a safety cutout bimetallic switch which is embedded in the warming device 22 cuts off all power to cassette 10. No audible alarm is heard and the temperature display goes blank. Suitable bimetallic switches are well known and available in the art.

The device can also operate by battery power to make the device truly portable.

Thus, to allow maximum user flexibility, especially important in emergency hospital care, a blood/fluid warming system is designed and provided in which the cassette 10 is easily inserted into slot 20 of warmer device 22. For proper operation, the cassette 10 should be inserted into the slot 20 so the first device 32 contacts the heating material 30 and the second device 31 contacts the cassette 10.

To assist the cassette be properly inserted into the slot 20, the cassette can have aligning guide rails 48a, b (as shown in FIG. 3c) that correspond with mating slots 220a, b, respectively, of device 22 as illustrated in FIG. 4. The cassette 10 is continued to be inserted into the slot 20 until the cassette can no longer be inserted therein. The stoppage of the cassette can be caused by a visual indicator 222 that projects from the opening 224 on the opposite side of the inlet/outlet 14, 18 side of the slot 20. Alternatively, the cassette 10 could have tubing 99 (as shown in FIG. 2) that forms a portion of the inlet 14 and outlet 18. The tubing 99 can stop the cassette 10 from being under-inserted and/or over-inserted into the slot 20.

Figure 5A:
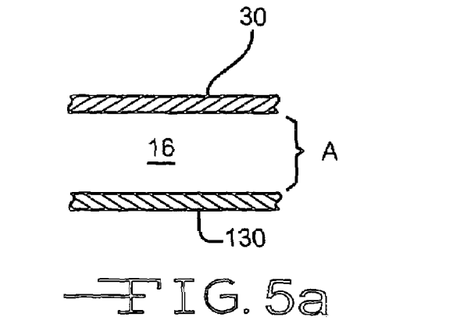
FIGS. 5a and b; 6a and b; and 7a and b illustrate embodiments in which to apply a force to the fluid contained in the fluid bag.
Figure 5B:
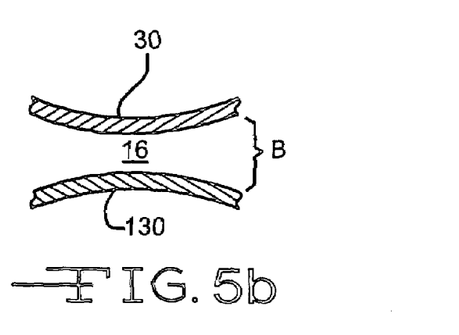
Figure 6A:
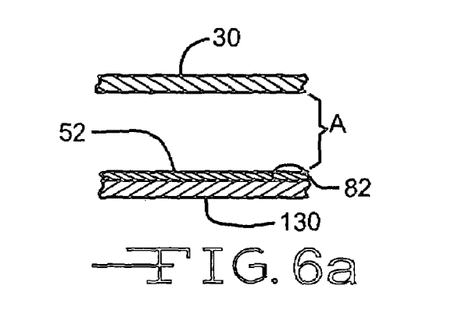
Figure 6B:
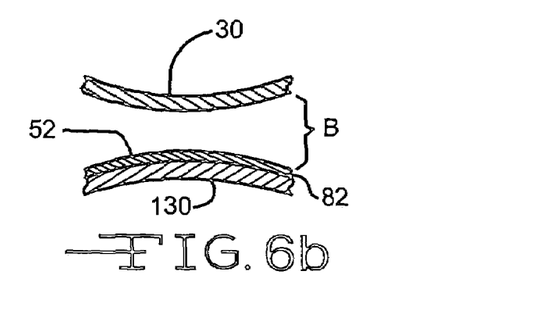

As indicated above, the heating element 30 is any material that creates the desired thermal energy to control the temperature of the fluid in the cassette and/or tubing when an electrical current is passed through the heating element and is capable of being integrated with the cassette 10 and tubing 99. The conductive material can also be an electromagnetic material. When an electrical current is passed through the material the electro-magnetic material acts as a magnetic material. The electromagnetic material receives the electrical current and generates the desired thermal energy and simultaneously is attracted to a corresponding magnetic or a second electromagnetic material (collectively referred to as the "other material") on the opposite side of the cassette 10. This embodiment is illustrated in comparison analysis of no current—FIGS. 5a and 6a—to current applied—FIGS. 5b and 6b. By opposite side of the cassette, we mean the other material 130 is either integrated with the cassette 10 opposite the conductive material 30 as illustrated in FIGS. 5a and b, or is a side or a portion of the surface that defines the slot as illustrated in FIGS. 6a and b. If the other material 130 is an electromagnetic material as illustrated in FIGS. 5a and b, the other material 130 receives an electrical current in the same way that the conductive material 30 receives its current.

When the conductive material 30 is pressed toward the other material 130, the conductive material 30 pushes the fluid toward the outlet by decreasing the size of the fluid path (compare A to B in FIGS. 5a and b, and 6a and b).

Figures 7A, 7B:
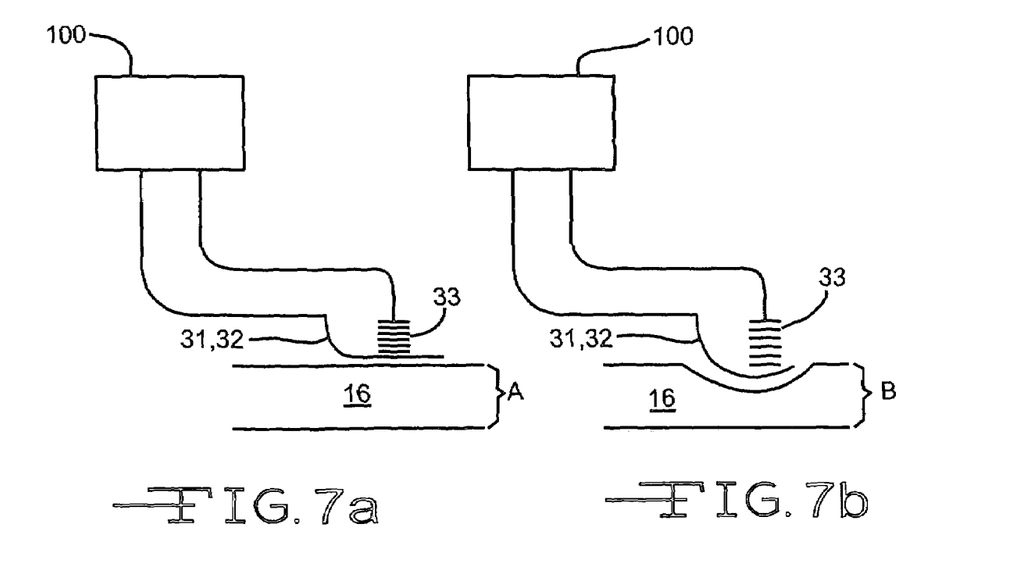

Alternatively, the various devices 31, 32 can be interconnected to a third device 33. The third device 33 is an actuator that applies a force (as illustrated in comparison FIGS. 7a and b—a downward force) to the devices 31, 32. When that force is applied, the devices 31, 32 push into the fluid path 16 (see analysis of A and B height differentials of the fluid path) to apply a forward force (seen by arrows) to exterior surface 17 of the cassette 10 to direct the fluid in the fluid path 16 toward the outlet 16. Alternatively, the third device 33 can directly apply the forward force to the exterior surface 17 of the cassette 10 to direct the fluid in the fluid path 16 toward the outlet 16. The timing of when the forward force is applied is controlled by the controlling device.

Figure 8:
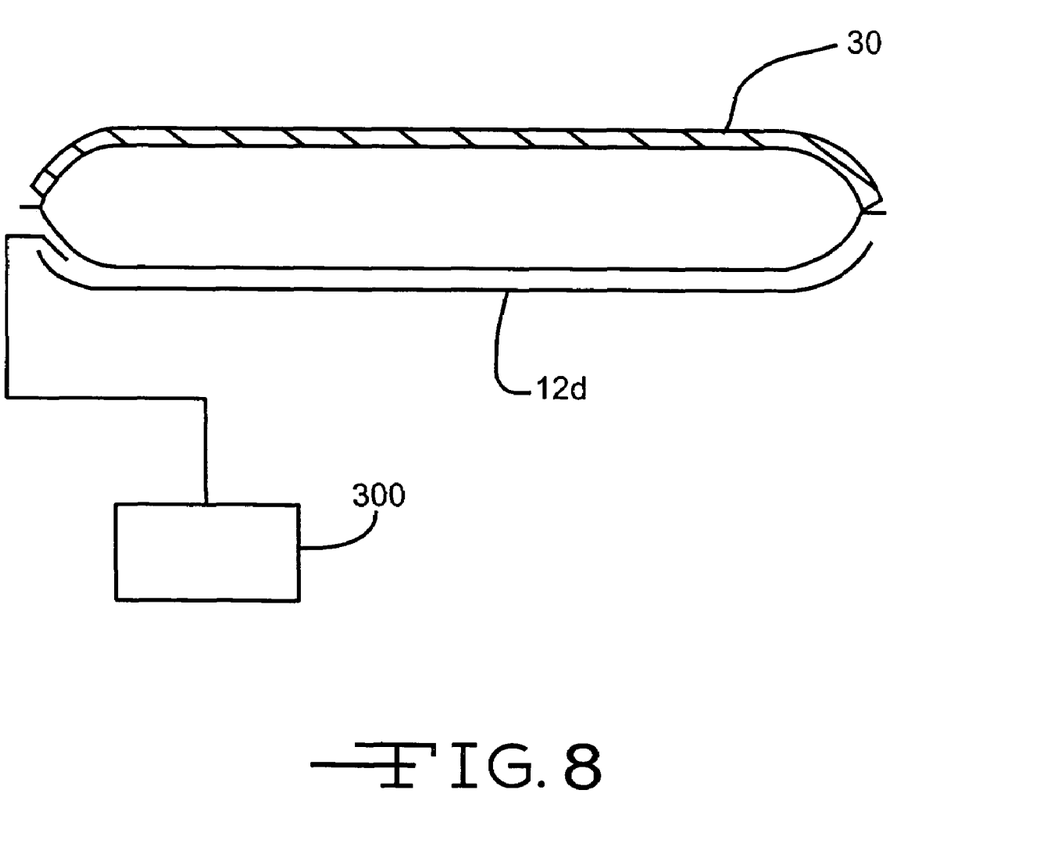
FIG. 8 is an alternative embodiment of FIG. 1.

In a further alternative embodiment, the cassette has a fourth fluid impermeable material 12d, as illustrated in FIG. 8. This fourth material 12d is on the opposite side of the cassette 10 which has the heater element 30 thereon, or alternatively on the same side, which means the fourth material 12d can be the third material or be positioned over the third material. The fourth material 12d can be sealed to the remaining cassette material (12; 12a,b; 12a,b,c) in the same manner in which the third material is sealed to the other materials. Preferably, the fourth material 12d is positioned to conform to the fluid path 16 and therefore has an inlet and an outlet that corresponds to the inlet 14 and outlet 18 of the fluid path. That way a second fluid can be injected into a compression path positioned between the fourth material 12*d* and the remaining cassette material (12; 12*a,b*; 12*a,b,c*).

The second fluid can be a gas or a liquid. Preferably, the second gas is either water or air. In any case, the second fluid is occasionally pumped through the compression path to direct the fluid in the fluid path toward the outlet. The second fluid can have any temperature. Preferably, the temperature of the second fluid corresponds with the temperature of the heater elements. Controlling the temperature of the second fluid and directing the second fluid into the compression path can be accomplished with conventional devices known to those of ordinary skill in the art.

The present warming device 22 can be positioned horizontally, vertically or any direction there between. The warming device 22 can be positioned anywhere that is needed because it can have various adaptations to attach it to the desired device and/or in any location.

Figure 9:
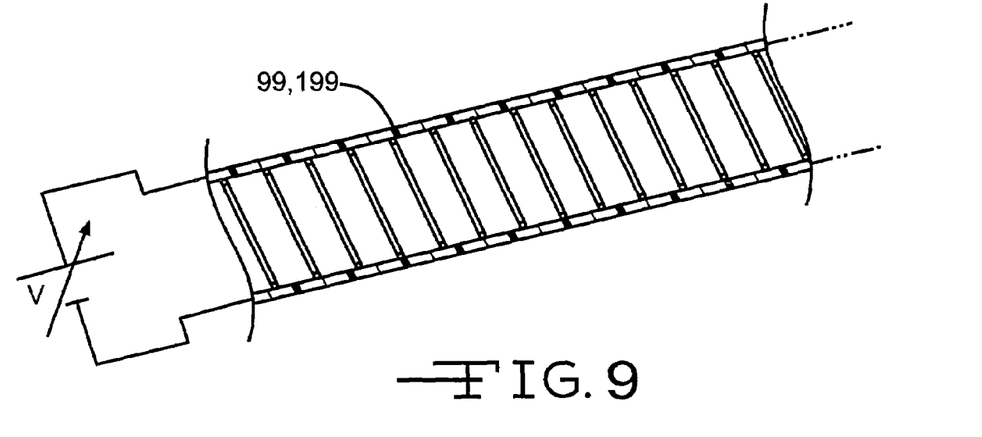
FIG. 9 is an alternative embodiment of FIG. 1.

Turning to FIG. 9, the heating element 30, as indicated previously above, can be wrapped in a cage-like manner (like chicken wire) or wire weave frame on the interior surface of the material (a.k.a., fluid path) for the tubing, within the tubing material, outside the delivery tube 99, 199, or combinations thereof (the latter is the catheter tube). This design ensures that the heated fluid from the cassette 10 retains its desired temperature into the patient. The heating element 30 in the tubes can be interconnected to the same energy source as the heating elements for the cassette, or alternatively to a second energy source which could be independent or dependent on the first energy source.

Figure 10:
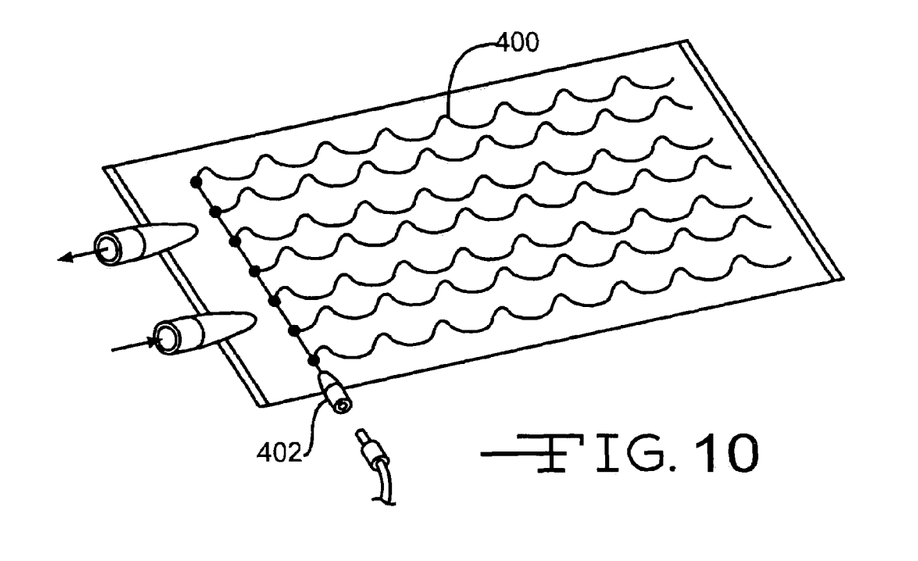
FIG. 10 is an alternative embodiment of FIG. 1.
Figure 10A:
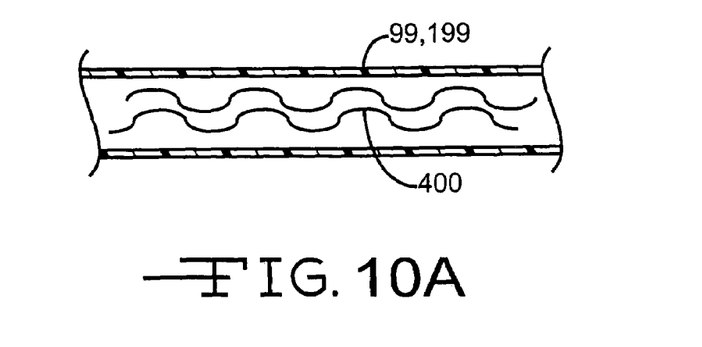

In addition to those alternative designs, the heating element can be shaped like streamers 400 as illustrated in FIG. 10 for the cassette 10 and/or the tubes 99, 199. This streamer design can be on the exterior surface of the material, within the material itself, on the interior surface (a.k.a., fluid path) of the material, or combinations thereof. This streamer design can increase the surface area of the heating element, and possibly eliminate the need for a gap for the cassette in the warming device. The electrical contact device 402 of the streamers can be an electrical/magnetic device positioned on and/or over the streamers. The electrical/magnetic device allows the cassette and/or tubes to contact the electrical source without the gap thereon. This electrical/magnetic device can be incorporated in the other embodiments of the present invention as well.

Having described the invention with regard to certain specific embodiments thereof, it is to be understood that this description is not meant as a limitation since further modifications may now suggest themselves to those skilled in the art, and it is intended to cover such modifications as fall within the scope of the appended claims.

We claim:

1. A fluid warming system comprising:
   a) a first fluid warming bag having (i) at least one fluid impermeable material that defines an inlet, an outlet, a top surface, a bottom surface, a fluid path extending between the inlet and the outlet, and (ii) a heating element integrated with the bag and positioned over a predetermined portion of the fluid path; and
   b) a warmer device having a slot and within the slot is a first actuating member, the first actuating member provides an electrical current to the heating element when the first fluid warming bag is inserted into the slot.

2. The fluid warming system of claim 1 wherein the heating element is integrated into or onto the bag by a method selected from the group consisting of printing, embossing, heat sealing, sonic sealing, adhesion, lithographing, or combinations thereof.

3. The fluid warming system of claim 1 wherein the fluid impermeable material permits thermal energy generated from the heating element to permeate into the fluid path.

4. The fluid warming system of claim 1 wherein fluid path has a design selected from the group consisting of a counterflow, a serpentine, a random, and a straight method.

5. The fluid warming system of claim 1 wherein the fluid impermeable material is at least two impermeable materials.

6. The fluid warming system of claim 1 wherein the fluid impermeable material is a polymeric material.

7. The fluid warming system of claim 1 further comprising a sensor that measures the temperature of the fluid in the fluid path.

8. The fluid warming system of claim 7 wherein the sensor is attached to a second actuating member.

9. The fluid warming system of claim 8 wherein the second actuating member extends from a surface of the slot toward the other surface of the slot.

10. The fluid warming system of claim 1 wherein the second actuating member is a predetermined surface of the slot.

11. The fluid warming system of claim 1 wherein the first actuating member is a predetermined surface of the slot.

12. The fluid warming system of claim 1 wherein the first actuating member extends from a surface of the slot toward the other surface of the slot.

13. The fluid warming system of claim 1 wherein the inlet comprises a tube.

14. The fluid warming system of claim 13 wherein the tube is a stop mechanism to prevent over-insertion of the bag into the slot.

15. A fluid warming system of claim 1 wherein the fluid warming bag has a front edge having the inlet, a back edge that is opposite the front edge and two side edges; and at or near each side edge is a guide rail.

16. A fluid warming system of claim 1 further comprising a compression path.

17. A fluid warming system of claim 1 comprising a compression force apparatus that applies a compression force to the fluid in the fluid path.

18. A fluid warming system of claim 17 wherein the compression force apparatus is selected from the group consisting of the first actuation device that provides the electrical current to the heating element, a second actuation device that comprises a temperature sensor for the fluid in the fluid path, a third actuation device that just applies the compression force to the fluid in the fluid path, an electromagnetic system with at least the heating element, or combinations thereof.

19. A fluid warming system of claim 17 wherein the compression force is intermittent.

20. A fluid warming system of claim 17 wherein the compression force is constant.

21. A fluid warming bag comprising:
   a) at least one fluid impermeable material that defines an inlet, an outlet, a top surface, a bottom surface, a fluid path extending between the inlet and the outlet, and
   b) a heating element integrated with the bag and positioned over a predetermined portion of the fluid path.
   c) a compression force apparatus that applies a compression force to said fluid impermeable material, causing the fluid in the fluid path to flow.

22. The fluid warming bag of claim 21 further comprising a warmer device having a slot and within the slot is a first actuating member, the first actuating member provides an electrical current to the heating element when the first fluid warming bag is inserted into the slot.

23. The fluid warming bag of claim 21 wherein the heating element is integrated into or onto the bag by a method selected from the group consisting of printing, embossing, heat sealing, sonic sealing, adhesion, lithographing, a conductive material for the bag itself, or combinations thereof.

24. The fluid warming bag of claim 21 wherein the fluid impermeable material permits thermal energy generated from the heating element to permeate into the fluid path.

25. The fluid warming bag of claim 21 wherein fluid path has a design selected from the group consisting of a counter-flow, a serpentine, a random and a straight method.

26. The fluid warming bag of claim 21 wherein the fluid impermeable material is at least two impermeable materials.

27. The fluid warming bag of claim 21 wherein the fluid impermeable material is a polymeric material.

28. The fluid warming bag of claim 22 further comprising a sensor that measures the temperature of the fluid in the fluid path.

29. The fluid warming bag of claim 28 wherein the sensor is attached to a second actuating member.

30. The fluid warming bag of claim 28 wherein the second actuating member extends from a surface of the slot toward the other surface of the slot.

31. The fluid warming bag of claim 22 wherein the second actuating member is a predetermined surface of the slot.

32. The fluid warming bag of claim 22 wherein the first actuating member is a predetermined surface of the slot.

33. The fluid warming bag of claim 22 wherein the first actuating member extends from a surface of the slot toward the other surface of the slot.

34. The fluid warming bag of claim 22 wherein the inlet comprises a tube.

35. The fluid warming bag of claim 34 wherein the tube is a stop mechanism to prevent over-insertion of the bag into the slot.

36. A fluid warming bag of claim 21 wherein the fluid warming bag has a front edge having the inlet, a back edge that is opposite the front edge and two side edges; and at or near each side edge is a guide rail.

37. A fluid warming bag of claim 21 further comprising a compression path.

38. A fluid warming bag of claim 21 comprising a compression force apparatus that applies a compression force to the fluid in the fluid path.

39. A fluid warming bag of claim 21 wherein the compression force apparatus is selected from the group consisting of the first actuation device that provides the electrical current to the heating element, a second actuation device that comprises a temperature sensor for the fluid in the fluid path, a third actuation device that just applies the compression force to the fluid in the fluid path, an electromagnetic system with at least the heating element, or combinations thereof.

40. A fluid warming bag of claim 21 wherein the compression force is intermittent.

41. A fluid warming bag of claim 21 wherein the compression force is constant.

42. A fluid warming bag of claim 6 wherein the polymeric material is conductive.

43. A fluid warming system comprising
a container that contains a fluid wherein the fluid is released from the container through a tube, the tube directs the fluid to a patient;
the tube has a heating element positioned on the interior surface of the tube so the heating element directly contacts the fluid, within the material that forms the tubing, on the exterior surface of the tube; or combinations thereof;
the heating element is interconnected to a power source that controls the temperature of the heating element which controls the temperature of the fluid.

44. The fluid warming bag of claim 21 wherein the heating element is streamer-like.

* * * * *